United States Patent [19]

Bailey

[11] Plant 4,855

[45] Jun. 8, 1982

[54] ROSE PLANT

[75] Inventor: Dorothy J. S. Bailey, Bakersfield, Calif.

[73] Assignee: San Joaquin Rose Co., McFarland, Calif.

[21] Appl. No.: 185,537

[22] Filed: Sep. 9, 1980

[51] Int. Cl.[3] ..... A01H 5/00

[52] U.S. Cl. ..... Plt./11

[58] Field of Search ..... Plt./11

*Primary Examiner*—James R. Feyrer

*Attorney, Agent, or Firm*—Vincent G. Gioia

[57] ABSTRACT

A new grandiflora rose variety of orange red to smoky red coloring, darkening to near currant red upon aging.

1 Drawing Figure

1

The present invention relates to a new and distinct variety of rose plant of the grandiflora rose class, which was originated by my crossing as seed parent the rose known as "Portrait" and the rose known as "Christian Dior" as pollen parent.

Among the novel characteristics possessed by this new variety which distinguish it from its parents and all other varieties of which I am aware are flowers of varying orange red and smoky red coloring borne on a vigorous disease resistant plant. The flower's unique coloring with light colored highlights darken upon aging to a more general red coloration. Flowers are exceptionally long lasting on the plant and as a cut flower. Asexual reproduction by budding of the new variety as performed in Kern County, Calif., shows that the foregoing and other distinguishing characteristics come true to form and are established and transmitted through succeeding propagations.

The new and improved rose variety which I have developed is an unusually fine grandiflora rose featuring unusual coloration as flowers mature and age and excellent substance which enable them to last very well on the plant and as cut flowers. The free branching plant has abundant foliage which is very disease resistant.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "46A" is plate 46A of the Royal Horticultural Society Color Chart.

Parentage: Seedling.

*Seed parent.*—"Portrait".

*Pollen parent.*—"Christian Dior".

Class: Grandiflora.

The following observations are made of specimens grown outdoors in Kern County, Calif. during the month of October.

1. FLOWER

Blooming habit: Recurrent.

A. Bud:

(1) *Size.*—Medium.

2

(2) *Form.*—Ovoid.

(3) *Color.*—When sepals first divide — Smoky Red 179A. When petals begin to unfurl — outer petals remain 179A but inner petals beginning to unfurl are lighter toned (179B) and petals show mixed coloration.

(4) *Sepals.*—Long pointed extending beyond bud.

(5) *Peduncle.*—Length — 3½ to 4 inches. Aspect — straight. Strength — erect, strong. Color — green.

B. Bloom:

(1) *Size.*—Average size when fully expanded — about 4 to 4½ inches.

(2) *Borne.*—Singly and several together.

(3) *Form.*—Short pointed bud opening to somewhat flat full flower.

(4) *Petalage.*—Number of petals under normal conditions — about 47.

(5) *Color.*—Smoky red buds open to reveal more orange red coloring. Outer petals tend to be darker colored, e.g. 179A; inner petals seem to be more orange red and lighter, however, the lighter color effect may be due to very light pink highlights more prevalent on the inner petals. The resulting mixed coloration in part resulting from color washing on individual petals gives an overall light centered appearance while blooms mature. But upon aging, the blooms settle into a more uniform "blackened" red coloring somewhat darker than 46A. The multi coloration during maturation is further emphasized by darker red petal edges washing into light red and pink.

C. Petals:

(1) *Texture.*—Medium to thick.

(2) *Appearance.*—Velvety to dull.

(3) *Form.*—Ovoid with slight cupping.

(4) *Arrangement.*—Imbricated.

(5) *Petaloids in center.*—Many, tend to conceal center of open bloom.

(6) *Persistence.*—Drop off cleanly.

(7) *Fragrance.*—Moderate, fruity.

(8) *Lasting quality.*—Long lasting on plant and as cut flower.

2. REPRODUCTIVE ORGANS

A. Stamens, filaments and anthers:

(1) *Arrangement.*—Regular, arranged around styles.

(2) *Color.*—5D.

B. Pollen:
*Color.*—9C.
C. Styles: Uneven, bunched.
D. Stigmas:
*Color.*—21C.
E. Hips:
*Shape.*—Globular.
*Size.*—Large.
*Color.*—Bright orange.
*Do seeds protrude?.*—Slightly.

3. PLANT

A. Form: Upright.
B. Growth: Vigorous, free branching.
*Height attained.*—About 3½ to 4 feet in first year.
C. Foliage: Compound 5 to 7 leaflets.
(1) *Size.*—Large.
(2) *Quantity.*—Abundant.
(3) *Color.*—New foliage: upper side — purple red deeper than 59A; under side — darker than 60A. Old foliage: upper side — near 137A; under side — near 137D.
(4) *Shape.*—Long, oval.
(5) *Texture.*—Upper side is leathery and under side is smooth, veined.
(6) *Edge.*—Serrate.

(7) *Serration.*—Simple.
(8) *Leaf stem.*—Color — bronze green. Under side — near 147C.
(9) *Stipules.*—Long, bearded.
(10) *Resistance to disease.*—Blackspot — excellent. Mildew — excellent. Rust — excellent.
D. Wood:
(1) *New wood.*—Color — apple green with red cast. Bark — smooth.
(2) *Old wood.*—Color — dark green near 146A with purple red cast. Bark — smooth.
E. Thorns:
(1) *Thorns.*—Quantity (main stalk): few. On laterals from stalk — few. Form — slightly rounded at base. Length — medium. Color — apple green. Position — regular.
(2) *Prickles.*—Very few.
F. Winter hardiness: Good winter hardiness.

I claim:

1. A new and distinct variety of rose plant of the grandiflora class, substantially as shown and described, characterized particularly by flowers of unusual multi-red toned coloration darkening upon aging to more uniform coloring.

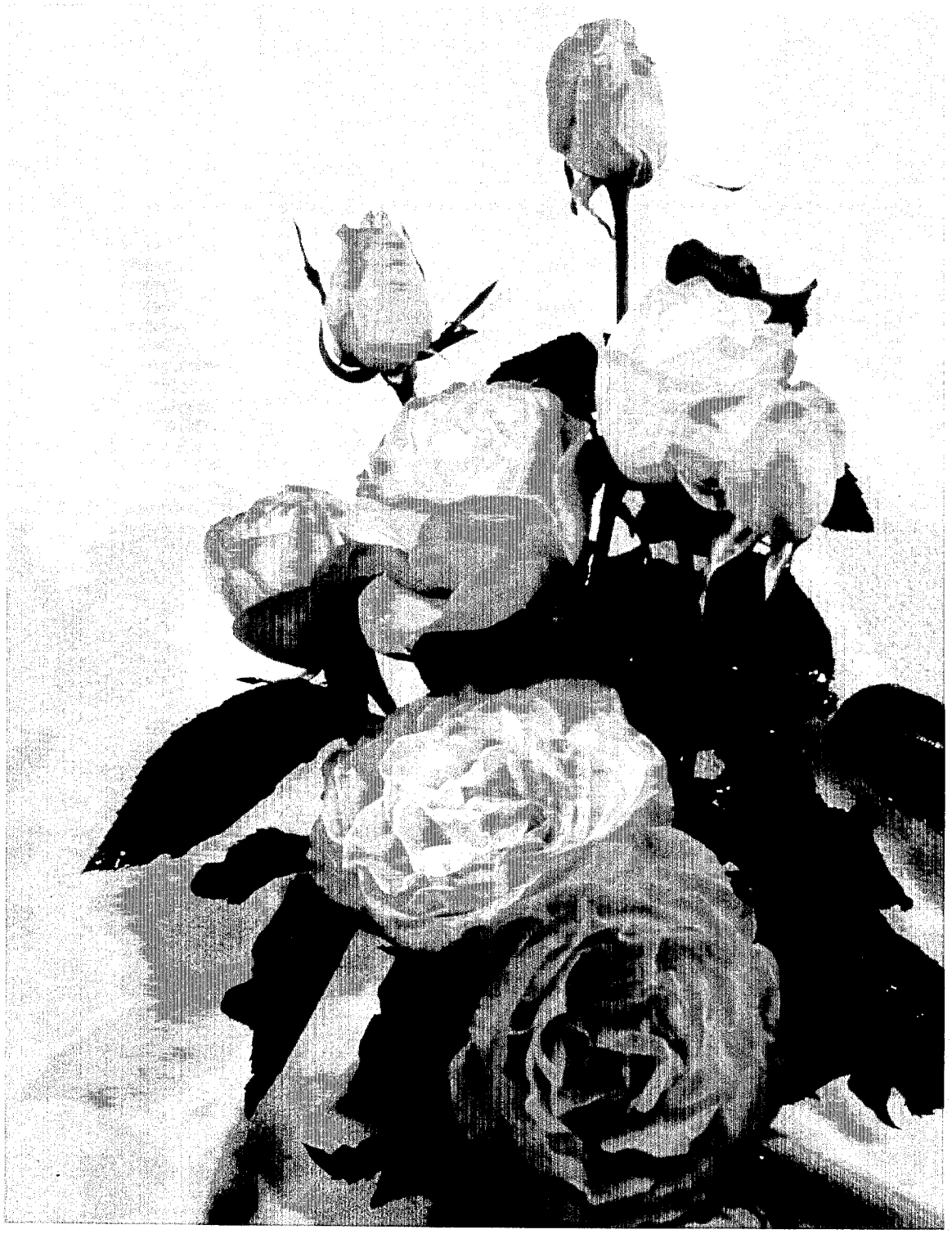

* * * * *